(12) United States Patent
Warner et al.

(10) Patent No.: US 9,693,702 B2
(45) Date of Patent: Jul. 4, 2017

(54) SYSTEM AND METHOD OF POTENTIAL EQUALIZATION MONITORING FOR MEDICAL DEVICES

(71) Applicant: GENERAL ELECTRIC COMPANY, Schenectady, NY (US)

(72) Inventors: Adrian Warner, Delafield, WI (US); Claudio Patricio Mejia, Chicago, IL (US); Daniel Richard Schneidewend, Menomonee Falls, WI (US); Rodger Schmit, West Bend, WI (US); Timothy Stiemke, West Bend, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 21 days.

(21) Appl. No.: 14/541,490

(22) Filed: Nov. 14, 2014

(65) Prior Publication Data

US 2016/0135884 A1    May 19, 2016

(51) Int. Cl.
| | |
|---|---|
| *A61B 18/00* | (2006.01) |
| *A61B 5/0432* | (2006.01) |
| *G01R 29/24* | (2006.01) |
| *A61B 5/0428* | (2006.01) |
| *A61B 18/12* | (2006.01) |
| *A61B 18/14* | (2006.01) |
| *A61B 5/00* | (2006.01) |

(52) U.S. Cl.
CPC .......... *A61B 5/0432* (2013.01); *A61B 5/0428* (2013.01); *A61B 18/1233* (2013.01); *G01R 29/24* (2013.01); *A61B 5/7203* (2013.01); *A61B 18/1492* (2013.01); *A61B 2018/00827* (2013.01); *A61B 2018/00839* (2013.01); *A61B 2018/00898* (2013.01)

(58) Field of Classification Search
CPC ................ A61B 18/16; A61B 18/1492; A61B 2018/162; A61B 2018/165; A61B 2018/167; A61B 2018/00827; A61B 5/04012; A61B 5/0432; A61B 5/044; A61B 5/0428; A61B 5/7203; A61B 18/1233; A61B 2018/00839; A61B 2018/00898; G01R 29/24
USPC .......................... 606/34, 35, 41, 42; 600/522
See application file for complete search history.

(56) References Cited

U.S. PATENT DOCUMENTS

| | | | |
|---|---|---|---|
| 2,381,527 A | 8/1945 | Traver | |
| 5,119,031 A | 6/1992 | Foulkes et al. | |
| 6,392,422 B1 | 5/2002 | Kammer et al. | |
| 8,150,520 B2 | 4/2012 | Demarais et al. | |
| 2009/0036885 A1* | 2/2009 | Gregg | A61B 18/1233 606/35 |
| 2009/0248007 A1* | 10/2009 | Falkenstein | A61B 90/90 606/33 |

(Continued)

*Primary Examiner* — Michael Carey
(74) *Attorney, Agent, or Firm* — Grogan, Tuccillo & Vanderleeden, LLP

(57) ABSTRACT

A method of potential equalization monitoring includes connecting a plurality of electrical devices to a patient, electrically connecting each of the plurality of electrical devices to a common equipotential grounding hub, the equipotential grounding hub defining a ground, monitoring a flow of current to the ground from at least one of the plurality of electrical devices, detecting a change in the balance of electrical charge between the plurality of devices, and identifying a source of the change in the balance of electrical charge.

19 Claims, 3 Drawing Sheets

(56) References Cited

U.S. PATENT DOCUMENTS

2012/0195078 A1* 8/2012 Levin ................ A61B 18/1233
363/50
2014/0088462 A1  3/2014 Mishelevich
2014/0107533 A1  4/2014 Mishelevich

* cited by examiner

SYSTEM AND METHOD OF POTENTIAL EQUALIZATION MONITORING FOR MEDICAL DEVICES

BACKGROUND

Technical Field

Embodiments of the invention relate generally to medical devices and, more specifically, to a system and method of potential equalization monitoring for medical devices.

Discussion of Art

During a medical procedure, any number of electrical medical devices may be connected to a patient at any given time throughout the duration of the procedure, as well as connected to one another through the patient. For example, common pieces of equipment often used during medical procedures may include an ECG monitor, an electrocautery device and a catheter having an ablation electrode connected to a radiofrequency energy source.

When attaching an electrical device to a patient, it is desirable that the devices, as well as the patient, are "floating" from a grounding standpoint (i.e., ungrounded) to prevent shocking or burning the patient during a surgery or other medical procedure. In particular, if all the devices and the patient are not floating, stray electrical currents from defective devices and the like may pass through the patient and dissipate through various pathways to the ground (e.g., through the ECG grounding lead, the operating room table and/or a physicians body, causing electrical shock. However, even when all the electrical devices within an operating room and the patient are floating, they may not all be "floating" to the same degree. Accordingly, there may exist a difference in electrical potential between the various devices and/or one or more of the devices and the patient, which can be a source of undesirable noise.

This difference in electrical potential between the various devices is typically resolved by connecting each electrical device to a common AC power source and connecting equipotential grounding lugs on the rear of each device to a common ground, sometimes referred to as a star point.

Throughout a procedure, with the addition and subtraction of devices, the equipotential ground current within the system may vary. If one device is grounded except at the dedicated common source, the grounding system forms a loop path through which current may flow. At times, excess charge may be introduced to the patient. This change in the balance of charge can lead to increased noise and other adverse effects, such as reduction in the amplifier dynamic range. As will be readily appreciated, noise may also effect the visibility and clarity of the electrogram. While existing systems are sufficient to mitigate the risk of shocking or burning a patient, such systems are simply not capable of determining the cause of the change in the balance of charge (i.e., the source of electrical charge), or where and how current is flowing between the various devices and the patient, making it difficult for a physician to diagnose and resolve noise issues within the system.

In view of the above, there is a need for a potential equalization monitoring system that is capable of diagnosing the source of increased isopotentials at a patient.

BRIEF DESCRIPTION

In an embodiment, a method of potential equalization monitoring is provided. The method includes the steps of connecting a plurality of electrical devices to a patient, electrically connecting each of the plurality of electrical devices to a common equipotential grounding hub, the equipotential grounding hub defining a ground, monitoring a flow of current to the ground from at least one of the plurality of electrical devices, detecting a change in the balance of electrical charge between the plurality of devices, and identifying a source of the change in the balance of electrical charge.

In an embodiment, a method of potential equalization monitoring includes electrically connecting a plurality of electrical devices to an equipotential grounding hub and monitoring a flow of current to the equipotential grounding hub from at least one of the plurality of electrical devices. The plurality of electrical devices and the equipotential grounding hub define an interconnected network. The method also includes the step of identifying an aberrant current flow within the network and determining a source of the aberrant current flow.

In an embodiment, a potential equalization monitoring system is provided. The system includes a first electrical device electrically connected to a patient, a second electrical device electrically connected to the patient, an equipotential grounding hub electrically connected to the first electrical device and the second electrical device, and a control unit electrically connected to the equipotential grounding hub. The control unit is configured to monitor a flow of current between the first electrical device, the second electrical device and the equipotential grounding hub to detect a change in the balance of electrical charge between the first device and the second device.

DRAWINGS

The present invention will be better understood from reading the following description of non-limiting embodiments, with reference to the attached drawings, wherein below:

DETAILED DESCRIPTION

Figure 1:
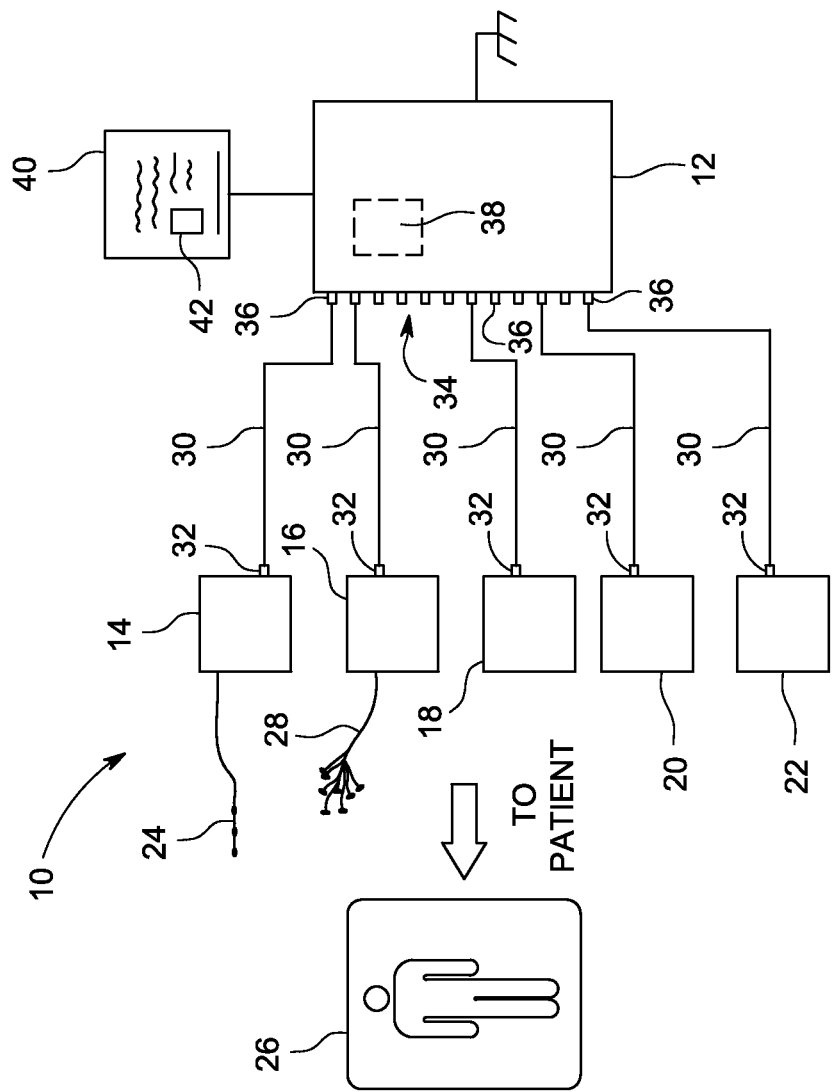
FIG. 1 is a schematic illustration of a potential equalization monitoring system in accordance with an embodiment of the present invention.

Reference will be made below in detail to exemplary embodiments of the invention, examples of which are illustrated in the accompanying drawings. Wherever possible, the same reference characters used throughout the drawings refer to the same or like parts. Although embodiments of the present invention are described as intended for use with interconnected medical devices and interfaces, it will be appreciated that embodiments may be adapted for use in connection with interconnected electrical devices, more generally. As used herein, "electrical contact," "electrical communication" and "electrically coupled" means that the referenced elements are directly or indirectly connected such that an electrical current may flow from one to the other. The connection may include a direct conductive connection (i.e., without an intervening capacitive, inductive or active element), an inductive connection, a capacitive connection, and/or any other suitable electrical connection. Intervening components may be present.

Referring now to FIG. 1, an embodiment of a potential equalization monitoring system 10 is depicted. As shown, the system 10 includes at least one electrical device electrically connected to an equipotential grounding hub 12. In an embodiment, the equipotential ground hub defines a common ground. In the example illustrated in FIG. 1, the at least one electrical device may be a plurality of electrical devices 14, 16, 18, 20 and 22 utilized in a medical procedure such as a cardiac or nervous system ablation procedure. In such an embodiment, the electrical devices 14, 16, 18, 20 and 22 may include a radiofrequency ablation device 14, an ECG recorder 16, a stimulation or pacing device 18, an ultrasound device 20 and an X-ray system 22. As will be readily appreciated, fewer or additional devices may be utilized in any given procedure depending upon the type of procedure and equipment needed.

The ablation device 14 may be any type of ablation device commonly known in the art, and generally includes a catheter 24 configured to be positioned within the body of a patient 26. The catheter 24 may be of any type commonly known in the art and typically includes an elongate body formed of an electrically insulating material, and having an ablation electrode (not shown) at its distal end. A plurality of ECG electrodes (not shown) are provided on the outer surface of the body.

In an embodiment, the recording device 16 may be an ECG device configured to monitor the electrical activity of the heart. The recording device 16 may therefore include an ECG cable 28 (such as a standard, 12-lead ECG cable) having a plurality of surface electrodes for attaching to the body of the patient 26. In an embodiment, the ECG device 16 may include, or be electrically connected to, an amplifier including a front end having a right-leg drive, of the type known in the art.

Moreover, in an embodiment, the stimulation or pacing device 18 may be any type of pacing device known in the art and configured to assist a physician to locate and pinpoint aberrant electrical pathways within the body of the patient 26. Likewise, the ultrasounds device 20 and the X-ray system 22 may be any type of such devices known in the art which are utilized by a physician to steer or navigate the ablation electrode on the catheter 24 to a target location within the body of the patient 26 where the ablation will be carried out, and to monitor, in real-time the location of the catheter 24 within the patient 26.

As will be readily appreciated, one ore of these devices may be placed in selective electrical communication with the patient 26 either continuously throughout a procedure or at intermittent times during the procedure. In an embodiment, these devices may be added or subtracted from the system 10 during a procedure, as necessary.

As further illustrated in FIG. 1, each electrical device 14, 16, 18, 20, 22 is electrically connected to the equipotential grounding hub 12 via a dedicated conductive lead 30 attached to each device. In particular, each electrical device 14, 16, 18, 20, 22 may include an equipotential lug bolt 32 protruding from the back thereof, to which one end of each lead 30 may be connected. The equipotential grounding hub 12 includes an array 34 of corresponding ports or lugs bolts 36 to which the opposite end of each lead 30 may be selectively connected. In this manner, a physician or operator may place any number of electrical devices in electrical communication with the hub 12 such that all the electrical devices within a room are coupled to a singular floating source.

As best shown in FIG. 1, the equipotential grounding hub 12 includes an integrated circuit 38 and sensing and control architecture configured to diagnose or determine the source of an electrical charge and a control unit or computer having a display device 40 for communicating information regarding the source of the electrical charge to a physician or operator and to aid in troubleshooting or resolving the source of the charge, as discussed in detail hereinafter. In an embodiment, the integrated circuit and sensing and control architecture may be integrated with the computer.

In operation, the equipotential leads 30 are connected to each electrical device 14, 16, 18, 20, 22 associated with a point of care relative to the patient 26. These devices 14, 16, 18, 20, 22 are then selectively connected to the hub 12 in the manner described above to establish a "star point" grounding scheme. Throughout a medical procedure, the integrated circuit 38 of the equipotential grounding hub 12 (which may, in an embodiment, may be part of the computer and display device 40) continuously monitors the current flowing to the hub 12. In particular, the control unit (e.g., the computer or integrated circuit) may sense or measure the current flowing within the network including the direction of flow, frequency, and the amount of current.

As will be readily appreciated, the ability to measure the ground current of each device provides faster and more precise capture of any change in the devices. In addition, in an embodiment, the system of the present invention provides for the monitoring of the right leg drive output on an ECG amplifier of the ECG device 18, which provides a further indication of excess charge being introduced to the patient 26.

As will be readily appreciated, this change in the balance of charge can lead to increased noise and reduction in the amplifier dynamic range. Monitoring both of these parameters, therefore, allows for triggers, display aids, audible alarms, measurement screens, trends, plots and other dynamic analytic methods to be employed to provide situational awareness. In addition, the monitoring provided by the system provides the ability to determine the causation of the change in current flow. In particular, once a change in the balance of charge is detected and/or monitoring of the right leg drive output indicates excess charge is being introduced to the patient 26, possible devices causing the change in current flow or excess charge may be displayed on display of the computer 40. As used herein, "balance of charge" means the flow of current from one device to another device. A change in the balance of charge may indicate aberrant current flow.

Moreover, in an embodiment, the computer and display 40, under control of a processor or control unit embodied in the computer 40, may suggest troubleshooting measures or prompt a user to go through a series of system checks to resolve the issue. For example, where ground current remains largely unchanged but the right leg drive output approaches saturation under, for instance, intracardiac ablation, may indicate a failure of the ablation pads attached to the patient, and so forth. Accordingly, the computer 40 may prompt a user to check that the ablation pads attached to the patient are properly positioned and adhered.

In an embodiment, the data collected by the computer 40 may be stored in a database 42 of the computer 40 and used with remote service functions such that automated service calls can be initiated, if required. The stored data may also be analyzed in a so-called 'big data' fashion to correlate events across an institution or product line by the manufacturer.

As will be readily appreciated, the system 10 of the present invention provides a physician with a situational awareness relative to the electrical system that is created by multiple electrical medical device being used to treat or diagnose a patient's condition. Understanding that a high ground current has been induced through the addition of a device, for example, may help identify the device that should be withdrawn from service before a routine service or maintenance event, or before failure. The ability to monitor the ground current and the right leg drive output can also indicate a systems issue which had manifested as noise in the patient's electrical.

By electrically connecting each electrical device to the equipotential grounding hub 12 and monitoring the current flow throughout the system, a number of advantages can be realized. In particular, the system 10 is configured to identify a change in the state of the system, detect and diagnose poor system performance, detect excess charge applied to a patient and determine the source from which the charge can be attributed, diagnose ground fault issues within the system as well as assess any ground loop effects. In addition, the system allows for the diagnosis and active management of system noise, which provides for clear and accurate readouts from electrical devices connected to the patient 26, such as the ECG recorder 16.

In contrast to the present invention, existing systems and methods are typically passive in nature. Indeed, while they may apply equipotential grounding but are incapable of understanding system performance, such as the direction, frequency, and source of currents, excess charges and the like. Accordingly, with existing devices, ground current and ground loops are often overlooked or missed. High ground current is often only determined at service. Moreover, right leg drive is typically not monitored and physicians are not aware of its functional performance except when noise is present in the system.

In an embodiment, rather than measuring the current at the point of connection to the equipotential hub 12, the system 10 may measure the ground current flowing to and from each device by monitoring each individual lead 30. Moreover, in an embodiment, the computer may be integrated with the hub to form an integrated potential equalization hub, control unit and display device.

Figure 2:
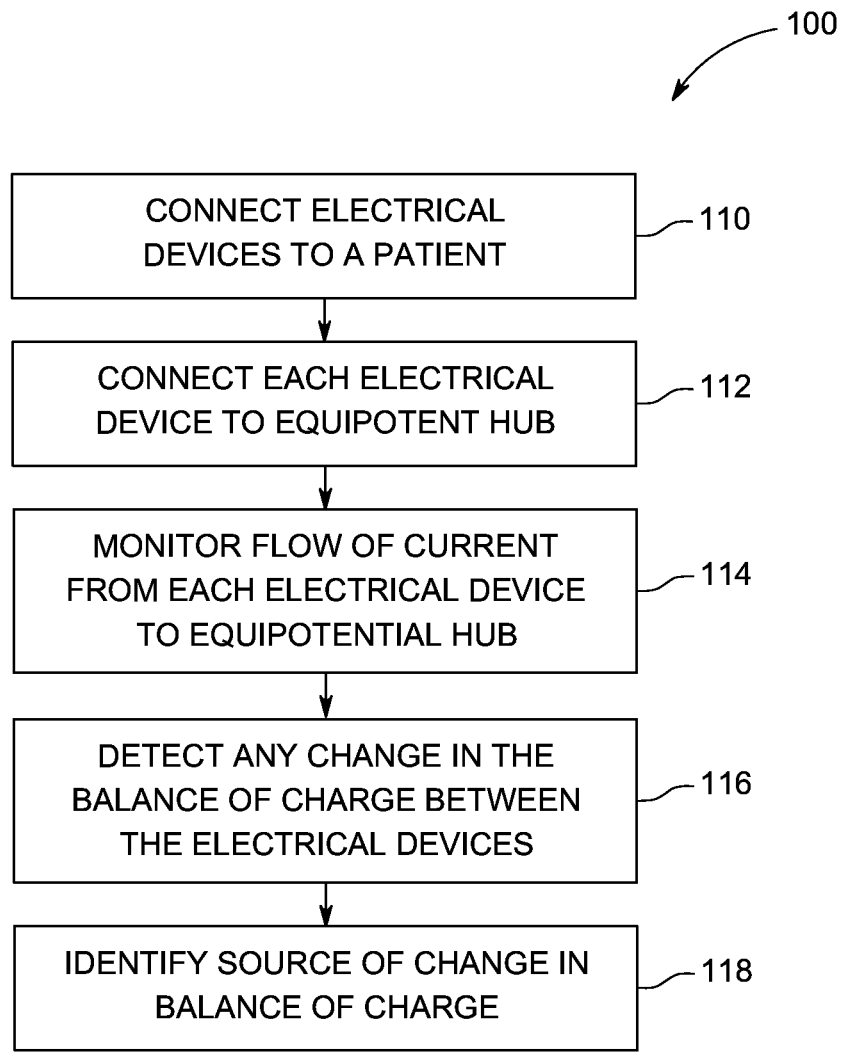
FIG. 2 is a flow diagram illustrating a method of potential equalization monitoring in accordance with an embodiment of the present invention.

Referring now to FIG. 2, an exemplary method of potential equalization monitoring is illustrated at 100. As shown therein, at step 110, a plurality of electrical devices are connected to a patient. Each of the electrical devices are then connected to a common equipotential grounding hub, as step 112. At step 114, the flow of current to the equipotential grounding hub from each of the electrical devices is monitored. At step 116, a change in the balance of the electrical charge between the devices is detected. Finally, at step 118, the source of the change in the balance of electrical charge is identified so that corrective action may be take to eliminate system noise or the like.

For example, in an embodiment, the electrical devices may include an ablation device and a recording device or ECG monitor, such as those utilized during cardiac or nervous system ablation procedures. During normal operation, the intended return source of current from the ablation device is from the catheter to the ablation pad (typically adhered to the back of a patient). By utilizing the method of the present invention, a physician may determine, for example, if current is flowing to the recording device, which is undesirable and may indicate a problem, burn a patient, or manifest as noise in the system. Once it is determined that there is a problem, the particular device can be identified and corrective action may be undertaken. For example, the system may then prompt a physician to check the devices and verify that the ablation pad is properly in contact with the skin of a patient.

Figure 3:
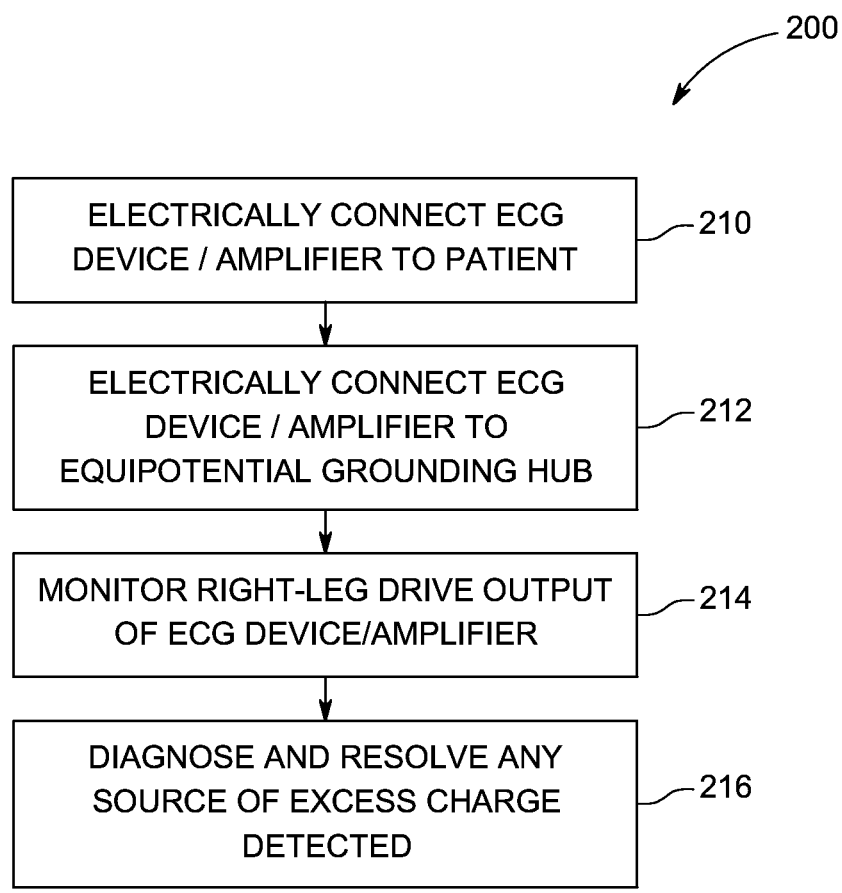
FIG. 3 is a flow diagram illustrating a method of potential equalization monitoring in accordance with another embodiment of the present invention.

With reference to FIG. 3, a method 200 of potential equalization monitoring according to another embodiment of the present invention is illustrated. As shown therein, at step 210, an ECG amplifier is electrically connected to a patient. At step 212 the ECG amplifier is electrically connected to an equipotential grounding hub. At step 214, the right leg drive output on the ECG amplifier is monitored in order to determine if excess charge is being introduced to the patient. Finally, if it is determined that excess charge is being introduced to the patient, the source of excess charged is diagnosed and resolved, at step 216.

While the present invention has been described above in connection with electrical devices utilized in a hospital setting or in a medical appreciated, it will be readily appreciated that the present invention is not so limited in this regard. In particular, it is contemplated that potential equalization and monitoring system of the present invention may be utilized with any type of electrical devices, irrespective of their intended use or configuration.

In an embodiment, a method of potential equalization monitoring is provided. The method includes the steps of connecting a plurality of electrical devices to a patient, electrically connecting each of the plurality of electrical devices to a common equipotential grounding hub, the equipotential grounding hub defining a ground, monitoring a flow of current to the ground from at least one of the plurality of electrical devices, detecting a change in the balance of electrical charge between the plurality of devices, and identifying a source of the change in the balance of electrical charge. In an embodiment, the step of detecting the change in the balance of electrical charge includes mapping the flow of current between the plurality of devices. In an embodiment, detecting the change in the balance of electrical charge includes measuring the flow of electrical charge between the plurality of devices and plotting the flow of electrical charge to obtain change in charge data. In an embodiment, the data may be stored in a database for future use. In an embodiment, an audible alarm may be generated if the change in the balance of electrical charge exceeds a threshold amount. In an embodiment, the method may also include the step of displaying information relating to the change in the balance of electrical charge to a user. The information may include identifying information indicating a particular device among the plurality of electrical devices that is the source of the change in the balance of electrical charge. In addition, in an embodiment, the information may include at least one troubleshooting step to be carried out by a user to resolve the change in the balance of electrical charge. In an embodiment, the plurality of devices include an ablation device having a catheter having an ablation electrode, and an ECG recording device, wherein the method may include detecting a change in the balance of electrical charge between the plurality of devices includes detecting a flow of current from the ablation device to the ECG recording device. In an embodiment, the troubleshooting step includes prompting the user to check if a grounding pad is properly attached to the patient. In an embodiment, one of the pluralities of electrical devices is an ECG amplifier, and wherein the method further includes the step of monitoring a right leg drive output on the ECG amplifier.

In an embodiment, a method of potential equalization monitoring includes electrically connecting a plurality of electrical devices to an equipotential grounding hub and monitoring a flow of current to the equipotential grounding hub from at least one of the plurality of electrical devices. The plurality of electrical devices and the equipotential grounding hub define an interconnected network. The method also includes the step of identifying an aberrant current flow within the network and determining a source of the aberrant current flow. In an embodiment, the method includes monitoring the flow of current includes measuring the flow of current between electrical devices and the equipotential grounding hub. In an embodiment, the step of monitoring the flow of current is carried out at the equipotential grounding hub. In an embodiment, each of the plurality of devices includes a lead in electrically communication with the equipotential grounding hub, and monitoring the flow of current includes monitoring each lead from the plurality of devices. In an embodiment, the aberrant current flow within the network is resolved under direction of a control unit. In an embodiment, one of the pluralities of electrical devices is an ECG amplifier, and the method further includes the step of monitoring a right leg drive output on the ECG amplifier.

In an embodiment, a potential equalization monitoring system is provided. The system includes a first electrical device electrically connected to a patient, a second electrical device electrically connected to the patient, an equipotential grounding hub electrically connected to the first electrical device and the second electrical device, and a control unit electrically connected to the equipotential grounding hub. The control unit is configured to monitor a flow of current between the first electrical device, the second electrical device and the equipotential grounding hub to detect a change in the balance of electrical charge between the first device and the second device. In an embodiment, the control unit is configured to identify a source of the change in the balance of electrical charge. In an embodiment, the first electrical device is an ECG amplifier and the control unit is configured to monitor a right leg drive output on the ECG amplifier. In an embodiment, the system includes a display electrically connected to the control unit and configured to display information relating to the flow of current.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope.

While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted based on 35 U.S.C. §122, sixth paragraph, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A method of potential equalization monitoring, comprising the steps of:
   connecting a plurality of electrical devices to a patient;
   electrically connecting each of the plurality of electrical devices to a common equipotential grounding hub, the equipotential grounding hub defining a ground;
   monitoring a flow of current to the ground from at least two or more of the plurality of electrical devices, via the equipotential grounding hub;
   detecting a change in the balance of electrical charge between the plurality of devices, via the equipotential grounding hub, and
   identifying a source of the change in the balance of electrical charge, via the equipotential grounding hub.

2. The method according to claim 1, wherein:
   detecting the change in the balance of electrical charge includes mapping the flow of current between the plurality of devices.

3. The method according to claim 2, wherein:
   detecting the change in the balance of electrical charge includes measuring the flow of electrical charge between the plurality of devices and plotting the flow of electrical charge to obtain change in charge data.

4. The method according to claim 3, further comprising the step of:
   storing the data in a database for future use.

5. The method according to claim 1, further comprising the step of:
   generating an audible alarm if the change in the balance of electrical charge exceeds a threshold amount.

6. The method according to claim 1, further comprising the step of:
   displaying information relating to the change in the balance of electrical charge to a user.

7. The method according to claim 6, wherein:
the information includes identifying information indicating a particular device among the plurality of electrical devices that is the source of the change in the balance of electrical charge.

8. The method according to claim 7, wherein:
the information includes at least one troubleshooting step to be carried out by a user to resolve the change in the balance of electrical charge.

9. The method according to claim 8, further comprising the step of:
storing the information in a database.

10. The method according to claim 8, wherein:
the plurality of devices include an ablation device having a catheter having an ablation electrode, and an ECG recording device; and
detecting a change in the balance of electrical charge between the plurality of devices includes detecting a flow of current from the ablation device to the ECG recording device.

11. The method according to claim 10, wherein:
the troubleshooting step includes prompting the user to check if a grounding pad is properly attached to the patient.

12. The method according to claim 1, wherein:
one of the plurality of electrical devices is an ECG amplifier; and
wherein the method further includes the step of monitoring a right leg drive output on the ECG amplifier.

13. A method of potential equalization monitoring, comprising the steps of:
electrically connecting a plurality of electrical devices to an equipotential grounding hub, the plurality of electrical devices and the equipotential grounding hub defining an interconnected network;
monitoring, via the equipotential grounding hub, a flow of current to the equipotential grounding hub from at least two or more of the plurality of electrical devices; and
identifying an aberrant current flow within the network and determining a source of the aberrant current flow, via the equipotential grounding hub.

14. The method according to claim 13, wherein:
monitoring the flow of current includes measuring the flow of current between electrical devices and the equipotential grounding hub.

15. The method according to claim 13, wherein:
each of the plurality of devices includes a lead in electrically communication with the equipotential grounding hub; and
wherein monitoring the flow of current includes monitoring each lead from the plurality of devices.

16. The method according to claim 13, further comprising the step of:
resolving the aberrant current flow within the network under direction of a control unit.

17. The method according to claim 13, further comprising the step of:
one of the plurality of electrical devices is an ECG amplifier; and
wherein the method further includes the step of monitoring a right leg drive output on the ECG amplifier.

18. A method of potential equalization monitoring, comprising the steps of:
connecting a plurality of electrical devices to a patient;
electrically connecting each of the plurality of electrical devices to a common equipotential grounding hub, the equipotential grounding hub defining a ground;
monitoring a flow of current to the ground from at least two or more of the plurality of electrical devices, via the equipotential grounding hub;
detecting a change in the balance of electrical charge between the plurality of devices, via the equipotential grounding hub; and
identifying a source of the change in the balance of electrical charge, via the equipotential grounding hub; and
wherein the monitored current is a ground current resulting from a buildup of charge within an electrical device connected to the patient.

19. A method of potential equalization monitoring, comprising the steps of:
connecting a plurality of electrical devices to a patient;
electrically connecting each of the plurality of electrical devices to a common equipotential grounding hub, the equipotential grounding hub defining a ground;
monitoring a flow of a ground current from at least two or more of the plurality of electrical devices to the ground, via the equipotential grounding hub;
detecting a flow of a stray current along an unintended path between two or more of the devices, via the equipotential grounding hub based at least in part on the monitored flow of the ground current; and
identifying a source of the stray current, via the equipotential grounding hub.

* * * * *